(12) United States Patent
Ueda et al.

(10) Patent No.: US 7,751,527 B2
(45) Date of Patent: Jul. 6, 2010

(54) MEASUREMENT METHOD OF LAYER THICKNESS FOR THIN FILM STACKS

(75) Inventors: Kazuhiro Ueda, Kawagoe (JP); Akio Yoneyama, Kawagoe (JP)

(73) Assignee: Hitachi, Ltd., Tokyo (JP)

( * ) Notice: Subject to any disclaimer, the term of this patent is extended or adjusted under 35 U.S.C. 154(b) by 43 days.

(21) Appl. No.: 12/292,178

(22) Filed: Nov. 13, 2008

(65) Prior Publication Data

US 2009/0180588 A1    Jul. 16, 2009

(51) Int. Cl.
*G03H 5/00* (2006.01)
(52) U.S. Cl. .................................... 378/36; 378/89
(58) Field of Classification Search .................. 378/36, 378/54, 70, 89, 90
See application file for complete search history.

(56) References Cited

U.S. PATENT DOCUMENTS 6,580,515 B1    6/2003  Li et al.
2005/0117699 A1    6/2005  Yoneyama

OTHER PUBLICATIONS

Albert, et al "Interferograms obtained with a X-ray laser by means of a wavefront division interferometer". Optics Communications, North-Holand Publishing Co., Amsterdam, NL, vol. 142, No. 4-6, Oct. 15, 1997, pp. 184-188.
L.G. Parratt, Surface Studies of Solids by Total Reflection of X-Rays, Physical Review, Jul. 15, 1954, vol. 95, No. 2, pp. 359-369, Cornell University, Ithaca, New York.
S.K. Sinha, et al., X-Ray and Neutron Scattering from Rough Surfaces, Physical Review, Aug. 1, 1988, vol. 38, No. 4, pp. 2297-2311, Corporate Research Science Laboratory, Exxon Research and Engineering Company, Clinton Township, Route 22 East, Annandale, New Jersey 08801.
Kenji Sakurai, et al., Fourier Analysis of Interference Structure in X-Ray Specular Reflection from Thin Films, Jpn. J. Appl. Phys. Feb. 1992, vol. 31 Part 2, No. 2A, pp. L113-L115.

*Primary Examiner*—Jurie Yun
(74) *Attorney, Agent, or Firm*—Antonelli, Terry, Stout & Kraus, LLP.

(57) ABSTRACT

Provided is a thin film stack inspection method capable of accurately measuring and inspecting layer thicknesses of thin film stacks. An X-ray having a long coherence length is used as an incident X-ray and the X-ray specular-reflected from a sample placed on a goniometer is partially bent by a prism. The X-ray bent by the prism and the X-ray going straight are made to interfere with each other to obtain interference patterns. Though being thin film stacks, the sample has a portion having no thin film and thus an exposed substrate. The X-ray not bent by the prism includes an X-ray specular-reflected from the exposed substrate. By changing the incident angle from 0.01° to 1°, the interference patterns of the specular-reflected X-ray are measured. Thus, layer thicknesses are measured using a change in a phase of the X-ray reflected from a film stack interface.

10 Claims, 4 Drawing Sheets

MEASUREMENT METHOD OF LAYER THICKNESS FOR THIN FILM STACKS

CLAIM OF PRIORITY

The present application claims priority from Japanese patent application JP 2008-007115 filed on Jan. 16, 2008, the content of which is hereby incorporated by reference into this application.

BACKGROUND OF THE INVENTION

1. Field of the Invention

The present invention relates to a method for nondestructively measuring each layer thickness of one or more thin film stacks stacked on a substrate.

2. Description of the Related Art

In the field of semiconductor devices and magnetic devices, for sophistication and performance improvement of elements, films to be formed have been made extremely thin and the number of the films to be stacked has also been increasing. Moreover, in a recent electronic device such as a semiconductor or magnetic device, control of film stack interfaces is also performed to control electron scattering at the film stack interfaces.

As a method for evaluating layer thicknesses of film stacks, ellipsometry and X-ray fluorescence analysis have heretofore been used. The ellipsometry is a method for obtaining a thickness and a refractive index of a sample thin film having a flat surface by making polarized light incident on the sample thin film and measuring a change in a polarized state of reflective light. However, since the ellipsometry uses light, the method has a problem that measurement cannot be performed unless the sample is transparent to light. The X-ray fluorescence analysis is a method for measuring fluorescence X-rays generated by a sample and estimating thicknesses on the basis of intensity of the X-rays. This method has the following problems. Specifically, only a total amount of elements generating the fluorescence X-rays is obtained and layer thicknesses are not directly measured. Moreover, when multiple thin films including the same elements are stacked, their layer thicknesses cannot be separately analyzed. Furthermore, neither the ellipsometry nor the X-ray fluorescence analysis can provide information on film stack interfaces.

Cross-section TEM observation for devices allows measurement of layer thicknesses of film stacks with very high spatial resolution and can also estimate interface widths. However, for the TEM observation, the sample needs to be divided into thin pieces of 100 nm or less, which leads to destructive analysis. Thus, although the TEM observation can be used for defect analysis, it is difficult to use the TEM observation for an inspection device.

X-ray reflectivity method is a method for nondestructively measuring layer thicknesses and interface widths of thin film stacks. The X-ray reflectivity method includes two kinds of methods. One is a method for making a monochromatic X-ray grazingly incident on a sample surface and measuring a reflectivity while changing an incident angle. The other one is a method for making a white X-ray incident on a sample and measuring wavelength dependence of a reflectivity. Both of the methods are for analyzing layer thicknesses by use of interference of the X-rays reflected from the sample surface and interface. Moreover, reflection from the surface or interface is influenced by the interface width. Thus, information on the interface widths of the film stacks can also be obtained by detailed analysis of an X-ray reflectivity profile. As a theoretical curve used for reflectivity analysis, used is a formula obtained by inserting the interface roughness effect of Sinha [Phys. Rev. B, 38, 2297 (1988)] into an explicit formula of Parratt [Phys. Rev., 95, 359 (1954). Moreover, for Fourier transform analysis, often used is a method by Sakurai et al. [Jpn. J. Appl. Phys., 31, L113 (1992).

SUMMARY OF THE INVENTION

The X-ray reflectivity method is an excellent method capable of evaluating the layer thickness and interface width of each film stack. However, in measuring a thickness of a very thin film, the thickness is obtained from a change in intensity of the reflective X-ray by changing the incident angle and changing a phase shift between the X-rays reflected from the surface and the interface. Thus, $2d \sin \theta = n\lambda$ holds and hence a significantly extended measurement range of the incident angle $\theta$ is required for measurement of an intensity change for one cycle. In measuring an oxide film with $d=0.5$ nm on a Si substrate, $\theta_{max} \approx 9°$ with $\lambda=0.154$ nm. The X-ray reflectivity is attenuated at $\exp\{-(q\sigma)^2\}$ ($\sigma$ is surface roughness) under the influence of the fourth power of a scattering vector size ($4\pi \sin \theta/\lambda$), and the surface roughness. This makes difficult to measure a wide range of $\theta$.

Moreover, for analysis of layer thicknesses or interface widths of a sample including a very thick film, an X-ray having high intensity and very high parallelism is required. A maximum layer thickness that a spectrometer using ++ arrangement of symmetry diffraction of Si (440) can measure is approximately 1 µm. Moreover, increase in layer thickness makes beam paths of the X-rays reflected respectively from the surface and the interface apart by a length longer than a coherence length. This lowers visibility of a vibrational structure and thus makes layer thickness analysis difficult.

Therefore, an object of the present invention is to provide an X-ray reflectivity method capable of measuring and inspecting layer thicknesses of film stacks including thin and thick films having thicknesses from subnanometer to several µm.

According to the present invention, layer thicknesses of film stacks are measured by measuring, with an X-ray interferometer, phase information on a reflective X-ray from a film stack sample and analyzing a phase reflectivity profile obtained.

According to an aspect of the present invention, an incident X-ray is partially bent by a prism and the X-ray bent by the prism and an X-ray going straight are allowed to interfere with each other. Moreover, in a wave front splitting interferometer for measuring interference patterns of the X-ray, a sample is placed on a goniometer in the interferometer, the sample having portions with and without thin film stacks. The X-ray reflected from the portion without film stacks is set as a reference wave and the X-ray reflected from the portion with the thin film stacks is set as an objective wave. By allowing the reference wave and the objective wave to interfere with each other, interference patterns are measured. Moreover, a phase of the objective wave is analyzed from intervals and positional shift between the patterns. In this event, it is also an aspect of the present invention to include, in the objective wave, a reflective X-ray from a region without film stacks. This is because of the following reason. Specifically, when the incident angle of the X-ray to the sample is changed, optical lengths of the reference wave and the objective wave are changed. Thus, it is impossible to distinguish between a change in the phase and a change in the optical length. Therefore, the change in the optical length is measured by use of the reflective X-ray from the substrate included in the objective wave and the phase change in film stacks is measured. The incident X-ray that can be used for the wave front splitting interferometer is preferably an X-ray having a coherence length of 10 μm or more.

Moreover, in the case of a phase reflectometer using an amplitude splitting interferometer, in addition to the use of a sample placed on the goniometer in the interferometer and having the portions with and without thin film stacks, it is required to return an optical path of the X-ray specular-reflected from the sample so as to allow the reference wave and the objective wave to have the same incident angle to a crystal tooth for combining the reference wave and the objective wave of the X-ray specular-reflected from the sample. It is also an aspect of the present invention to provide a reflector for returning the optical path.

Next, description will be given of an analysis method. In the case of a small layer thickness, an incident angle θ of an X-ray is allowed to satisfy all reflection conditions. Thus, an objective wave includes an X-ray reflected from a substrate and an X-ray reflected from a film stack surface. In this case, measured is a shift between an interference pattern in a region of the X-ray reflected from substrate and an interference pattern in a region of the X-ray reflected from film stacks. Assuming that the shift is ΔL and a width of the interference pattern for one cycle is L, a layer thickness d is expressed by the following equation (1) with a wavelength of the incident X-ray as λ.

$$d = \frac{\lambda}{2\sin\theta}\left(\frac{\Delta L}{L}\right) \quad (1)$$

Moreover, when the interference pattern is shifted more significantly than $2\pi$, ΔL can no longer be accurately measured. In this case, when interference patterns are measured at incident angles $\theta_1$ and $\theta_2$ and a shift between the interference patterns is set as ΔL, the layer thickness can be obtained by the following equation (2).

$$d = \frac{\lambda}{2(\sin\theta_1 - \sin\theta_2)}\left(\frac{\Delta L}{L}\right) \quad (2)$$
$$\approx \frac{\lambda}{2\Delta\theta \cdot \cos\theta_{av}}\left(\frac{\Delta L}{L}\right)$$

$\theta_{av}$ in the equation (2) is an average value of the two incident angles used for measurement and Δθ is a difference between the two incident angles.

Next, description will be given of a method for analyzing multi-layer stacks. Interference patterns are measured using a change of an incident angle θ to a sample from an angle smaller than a total reflection critical angle to about 1°. Thereafter, measured is a shift between an interference pattern in a region of the X-ray reflected from substrate and an interference pattern in a region of the X-ray reflected from film stacks. Thus, a phase shift between the X-ray reflected from the substrate and the X-ray reflected from the film stacks is obtained. This processing is performed for each incident angle of measurement to obtain incident angle dependence of a phase change in the film stacks. A reflectivity curve of the X-ray specular-reflected from the film stacks is represented as an explicit formula by Parratt [Phys. Rev., 95, 359 (1954)].

Assuming that an incident angle to the film stacks is θ, a wavelength of the incident X-ray is λ, a thickness of a j-th layer in the film stacks is $d_j$ and a refractive index is obtained as follows, $$n = 1-(\delta_j + i\cdot\beta_j) = 1-\{\lambda/(4\pi)\}^2(\xi + i\cdot\eta)$$

the reflectivity of the X-ray specular-reflected from the film stacks can be calculated by use of the following equations.

$$R_j = a_j^4 \frac{R_{j+1} + F_{j,j+1}}{R_{j+1} \cdot F_{j,j+1}} \quad (3)$$

$$\gamma_j^2 = q^2 - 2(\xi + i\eta_j) \quad (4)$$

$$a_j = \exp\left[-i\frac{\gamma_j \cdot d_j}{4}\right] \quad (5)$$

$$F_{j,j+1} = \frac{\gamma_j - \gamma_{j+1}}{\gamma_j + \gamma_{j+1}} \quad (6)$$

Normally, the X-ray reflectivity is measured by intensity and thus is obtained with $|R_1|^2$. However, in the case of use of the phase reflectometer, the phase of the reflective X-ray is obtained. Thus, by calculating $R_1$, comparison with an experimental value can be made. The equation (3) can be expressed as the following equations (7) and (8) since approximation of $\gamma_j \approx q$ can be made in regions of $q^2 >> \xi$ and $q^2 >> \eta$ and thus $|R_{j+1} \cdot F_{j,j+1}| << 1$ is satisfied.

$$R_j = a_j^4(R_{j+1} + F_{j,j+1}) \quad (7)$$

$$R_1 = \sum_{j=1}^{N}\left[\prod_{k=1}^{j}(a_k^4)F_{j,j+1}\right] \quad (8)$$

$F_{j,j+1}$ is a Fresnel coefficient for reflection and represents amplitude of a reflective wave, and $a_k$ represents a phase. The equation (8) shows that the phase reflectivity $R_1$ is addition of waves of the X-rays reflected from interfaces. By applying, to the equation (8), information on the phase measured by changing the incident angle, the phase of the X-ray reflected from each interface is obtained. Thus, $a_j$ can be solved by simultaneous equations. Consequently, thicknesses of the layers can be obtained.

As described above, the use of the phase reflectometer of the present invention enables a thin film stack inspection method.

According to the present invention, in a sample in which a protection film having a thickness of several μm or more and a liquid layer are stacked on film stacks, X-ray reflectivity from internal film stacks can be measured by reducing influences of the protection film layer or the liquid layer. Thus, layer thicknesses of the internal film stacks can be inspected with high accuracy.

DETAILED DESCRIPTION OF THE PREFERRED EMBODIMENTS

With reference to the drawings, an embodiment of the present invention will be described below.

Figure 1:
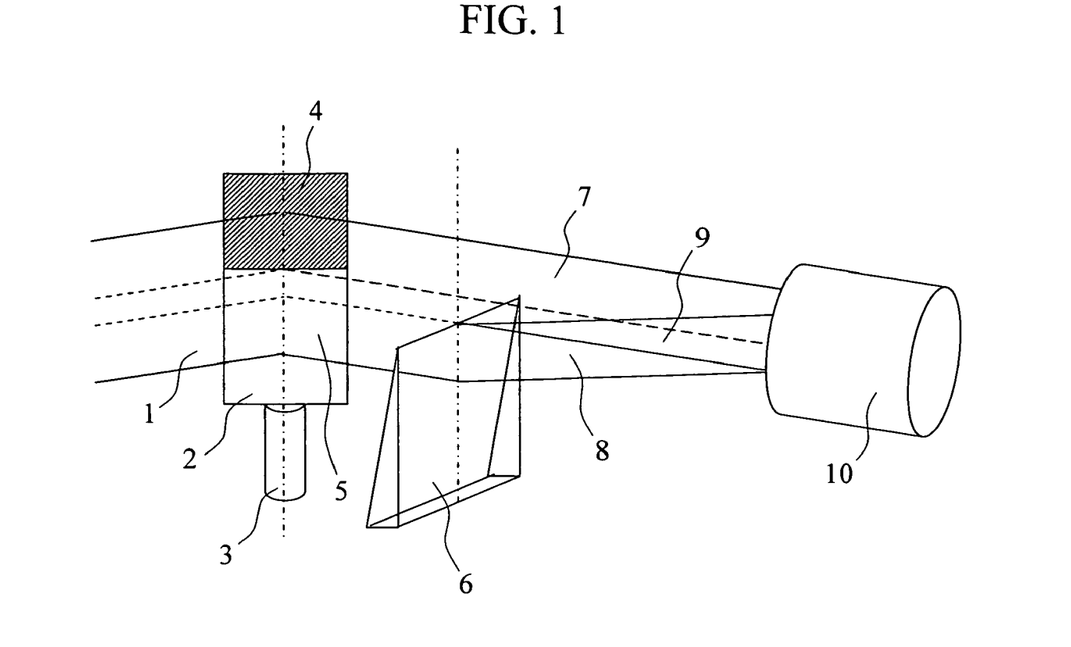
FIG. 1 shows an embodiment of the present invention.

FIG. 1 shows the embodiment of the present invention. An undulator synchrotron radiation source in a synchrotron radiation experiment facility (SPring-8) at Japan Synchrotron Radiation Research Institute is used as an X-ray source. An X-ray from the X-ray source is converted into a monochromatic X-ray having a wavelength of 0.1 nm by a monochrometer. After being formed into a shape of 100 μm in a z-direction and 50 μm in a y-direction by use of a slit, the X-ray is transmitted through an ion chamber for monitoring incident intensity and then irradiated onto a sample 2 as an incident X-ray 1. The sample 2 has a substrate obtained by sputter-depositing gold in a thickness of 3 μm on a silicon thin plate. Moreover, on the substrate, ruthenium is deposited in a thickness of about 1 nm as a thin film to be measured in film stacks 4. In an exposed substrate 5 having no ruthenium deposited therein, the gold film is exposed. When the gold is deposited in the thickness of about 3 μm, the gold film can be treated the same as a gold substrate since the X-ray does not reach the silicon therebelow. The sample 2 is fixed on a sample goniometer 3 and adjusted so as to make the incident X-ray 1 incident on the sample 2 at 0.3°. The incident X-ray 1 made incident on the sample 2 at 0.3° is totally reflected from the sample 2. The totally reflected X-ray includes a reflective X-ray from the film stacks 4 and a reflective X-ray from the exposed substrate 5. The reflective X-ray from the exposed substrate 5 is partially refracted by use of an acrylic prism 6 and thus is wavefront-split to obtain a reference wave 8. The reflective X-ray not transmitted through the prism is set to be an objective wave 7. The objective wave 7 includes a reflective objective wave from the film stacks 4 and a reflective objective wave 9 from the exposed substrate 5. At a position where the objective wave 7 and the reference wave 8 overlap with each other, a high-resolution two-dimensional detector 10 (for example, a zooming tube) is placed to measure interference patterns.

Figure 5:
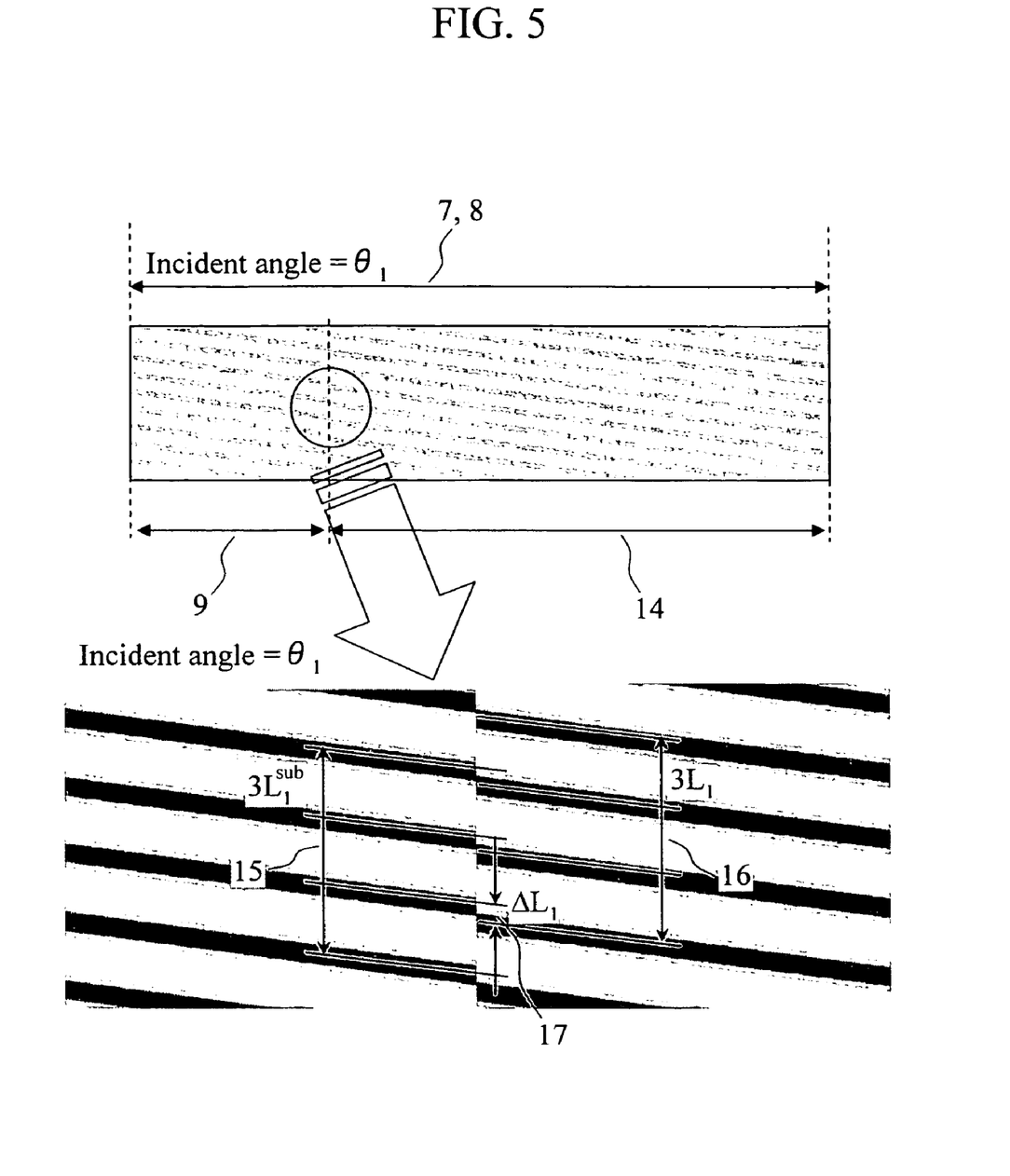
FIG. 5 is a schematic diagram of interference patterns when a thin film sample is measured according to the present invention.

FIG. 5 shows a schematic diagram of an interference pattern to be obtained. The objective wave 7 and the reference wave 8 overlap with each other to form interference patterns. The interference patterns formed differ between a reflective objective wave 14 from film stacks and the reflective objective wave 9 from the substrate. One cycle of shading of the interference pattern corresponds to a wavelength 0.1 nm of the X-ray. Specifically, a three cycle length 15 of the interference pattern for the reflective X-ray from exposed substrate is 0.3 nm and a three cycle length 16 of the interference pattern for the reflective X-ray from film stacks is also 0.3 nm. A difference in level between the both patterns is a phase shift 17 caused by the film stacks. In the case of this sample, the phase shift 17 is set to 0.09 when normalized by one cycle length of the interference pattern. Calculation of $d=\Delta L (\lambda/2 \sin \theta)$ according to the equation (1) leads to d=0.859 nm. Thus, it is found out that a film thickness of the ruthenium deposited is 0.859 nm.

However, it is difficult to accurately determine an incident angle. In such a case, a method for measuring the interference patterns with two incident angles is advantageous. However, although a change in the incident angle causes no problem as long as the positions of the prism and detector can be adjusted so as to match optical lengths with sub-Å accuracy, the optical lengths cannot be controlled with such accuracy in actual measurement. Therefore, in this embodiment, since the reflective objective wave 9 from the substrate and the reference wave 8 are known, a positional shift between this interference pattern and the interference pattern of the reflective objective wave 14 from film stacks is utilized to offset a shift in the optical path when the angle is changed.

Figure 6:
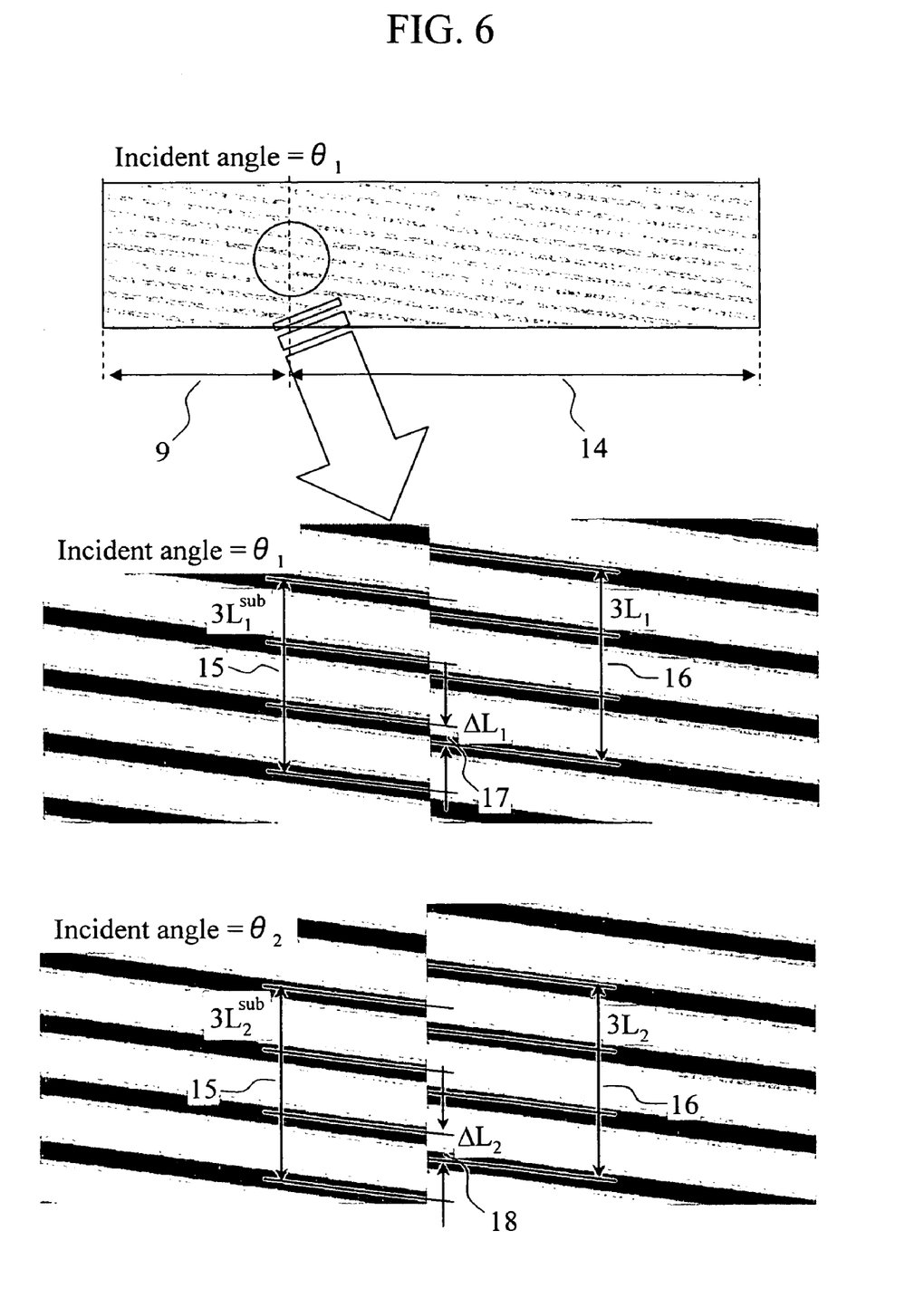
FIG. 6 is a schematic diagram of interference patterns when a thin film sample is measured according to the present invention.

FIG. 6 schematically shows a result of measurement with an incident angle $\theta_2=0.4°$ besides the result of measurement with the incident angle $\theta_1=0.3°$ as shown in FIG. 5. The wavelength of the incident X-ray is not changed even when the incident angle is changed. Thus, a three cycle length 15 of the interference pattern for the reflective X-ray from exposed substrate is 0.3 nm and a three cycle length 16 of the interference pattern for the reflective X-ray from film stacks is also 0.3 nm. However, since the incident angle is changed, a phase shift 18 in the incident angle of $\theta_2$ is not the same as the phase shift 17 in the incident angle of $\theta_1$. Since $(\Delta L_2/L_2)=0.12$, $\Delta L$ in the equation (2) is 0.03 and d=0.859 nm can be obtained by calculation according to the equation (2).

Figure 2:
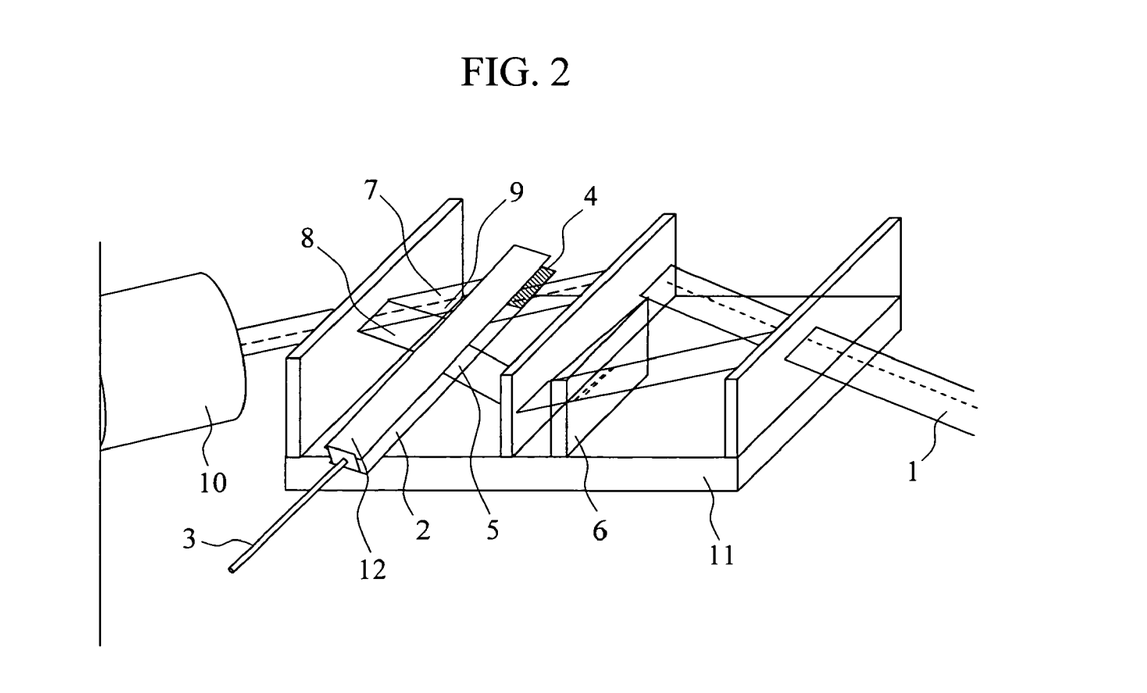
FIG. 2 shows another embodiment of the present invention.

Next, another embodiment will be described with reference to FIG. 2. A bending magnet synchrotron radiation source in a synchrotron radiation experiment facility (PF) at High Energy Accelerator Research Organization is used as an X-ray source. An X-ray from the X-ray source is converted into a monochromatic X-ray having a wavelength of 0.1 nm by a monochrometer. After being formed into a shape of 100 μm in a z-direction and 50 μm in a y-direction by use of a slit, the X-ray is transmitted through an ion chamber for monitoring incident intensity and then irradiated onto an amplitude splitting interferometer 11 made of Si single crystal as an incident X-ray 1. This interferometer includes three teeth, including a splitting device for splitting amplitude of the X-ray, a reflecting device for changing a direction thereof, and a combining device for allowing waves of the X-ray to interfere with each other. Thus, interference patterns can be obtained from the X-ray without a long coherence length as in the case of the embodiment described above.

The X-ray split by the first tooth has its direction changed by the second tooth. Thereafter, the X-ray is irradiated onto a sample 2 disposed between the second and third teeth. The sample 2 has a substrate obtained by sputter-depositing gold in a thickness of 3 μm on a silicon thin plate. Moreover, on the substrate, ruthenium is deposited in a thickness of about 1 nm as a thin film to be measured in film stacks 4. In an exposed substrate 5 having no ruthenium deposited thereon, the gold film is exposed. When the gold is deposited in the thickness of about 3 μm, the gold film can be treated same as a gold substrate since the X-ray does not reach the silicon therebelow. The sample 2 is fixed on a sample goniometer 3 and adjusted so as to make the incident X-ray 1 incident on the sample 2 at 0.6°. The incident X-ray 1 made incident on the sample 2 at 0.6° is specular-reflected from the sample 2. The specular-reflected X-ray is specular-reflected again from a reflection mirror 12 having gold deposited in a thickness of about 5 μm on a silicon substrate.

Figure 3:
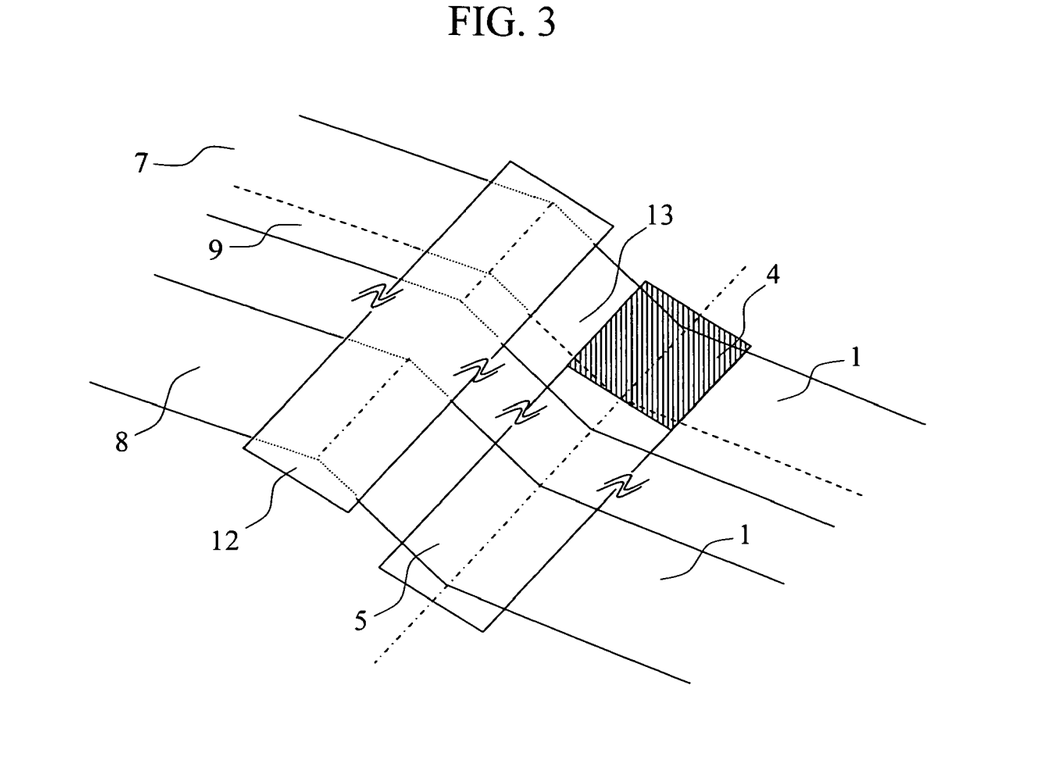
FIG. 3 is an enlarged view around a sample in FIG. 2.

FIG. 3 shows an enlarged view of the sample portion. One of the amplitude-split incident X-rays 1 is reflected from exposed substrate 5 of the sample 2 and then reflected again from the reflection mirror 12. Thus, a reference wave 8 is obtained. The other amplitude-split incident X-ray 1 is reflected from the exposed substrate 5 and a film stacks 4 of the sample. This reflective wave 13 is also reflected again from the reflection mirror 12 to obtain an objective wave 7. This objective wave 7 includes a reflective objective wave 14 from the film stacks and a reflective objective wave 9 from the exposed substrate. In the case of this embodiment, if there is no reflection mirror 12, the X-ray reflected from the sample 2 travels upward and the reference wave 8 and the objective wave 7 are made incident on the third tooth at slightly different angles. The incident angles at the third tooth need to match at the nanoradian level, since the reference wave 8 and the objective wave 7 have to interfere with each other. Thus, in this embodiment, the reflection mirror 12 is used to adjust the reflective X-ray so as to travel parallel to the incident X-ray 1. Consequently, the reference wave 8 and the objective wave 7 are allowed to interfere with each other at the third tooth.

In this event, if the reference wave 8 and the objective wave 7 are allowed to interfere with each other without making any adjustment, the same phase shift is set on the entire surface. Thus, there arises a situation where interference patterns are not visible. Therefore, by providing an acrylic prism 6 as a phase shifter on an optical path of the reference wave 8, the interference patterns can be obtained even in a state where there is no sample. The objective wave 7 and the reference wave 8 are allowed to overlap with each other by the third tooth, and the interference patterns are measured by use of a high-resolution two-dimensional detector 10 (for example, a zooming tube).

In this embodiment, with reference to FIG. 6, description will be given of an analysis method in the case where the incident angle is larger than a critical angle. In this embodiment, more measurement points than the number of interfaces included in the film stacks are required. The sample here is a 1-nm ruthenium thin film and there are interfaces above and below the ruthenium film. Thus, it is required to perform measurement with two incident angles larger than the critical angle. Therefore, $\theta_1$ is set to 0.6° and $\theta_2$ is set to 1°. Moreover, in the measurement, it is important to offset a change in an optical length due to a change in the incident angle by setting a phase of the reflective objective wave 14 from the film stacks to have a relative value to the reflective objective wave 9 from the exposed substrate. In this embodiment, $(\Delta L_2 - \Delta L_1)/L$ is 0.120. Since the incident angle is larger than the critical angle, phase information on interference between the X-rays reflected from a film stack interface and a film stack surface is recorded on the reflective objective wave 14 from film stacks. According to the equation (8), an amplitude reflectivity is obtained as $R_1 = F_{1,2} + F_{2,3} \cdot \exp[-i \cdot d \cdot q]$ and q-dependence of the amplitude reflectivity is obtained as $\cos[d \cdot q + C] + i \cdot \sin[d \cdot q + C]$. $(\Delta L_2 - \Delta L_1)/L$ of the measured interference pattern is set the same as $2 \cdot d \cdot (\sin\theta_2 - \sin\theta_1)/\lambda$, which is thus the same as the equation (2). By use of the equation (2), the film thickness of the ruthenium is obtained as d=0.860 nm. Moreover, even if the number of layers to be stacked is increased, each layer thickness can be obtained by the same analysis. Normally, the X-ray reflectivity is measured from a low angle region from which no X-ray from the sample runs off, in many cases, about 0.01° to about 1° at which the X-ray reflectivity is attenuated to about $10^{-6}$ and it becomes difficult to distinguish between the background and the reflective X-ray. Thus, multiple measurement angles to be measured in this embodiment are within a range of 0.01° to 1°.

As described above, this embodiment enables measurement of the phase of the reflective X-ray and analysis of layer thicknesses of the film stacks.

Figure 4:
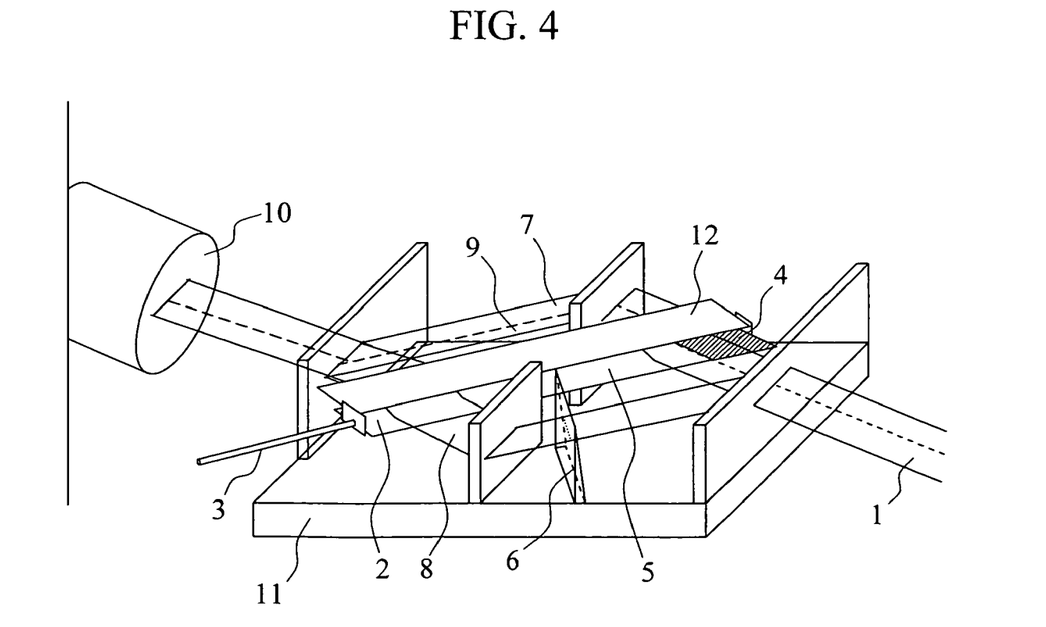
FIG. 4 shows another embodiment of the present invention.

Furthermore, another embodiment will be described with reference to FIG. 4. A bending magnet synchrotron radiation source in a synchrotron radiation experiment facility (PF) at High Energy Accelerator Research Organization is used as an X-ray source. An X-ray from the X-ray source is converted into a monochromatic X-ray having a wavelength of 0.1 nm by a monochrometer. After being formed into a shape of 100 μm in a z-direction and 50 μm in a y-direction by use of a slit, the X-ray is transmitted through an ion chamber for monitoring incident intensity and then irradiated onto an amplitude splitting interferometer 11 made of silicon single crystal as an incident X-ray 1. This interferometer includes three teeth, specifically for splitting amplitude of the X-ray, for changing a direction thereof, and for allowing waves of the X-ray to interfere with each other. Thus, interference patterns can be obtained from the X-ray without a long coherence length as in the case of the embodiment described above. The X-ray split by the first tooth has its direction changed by the second tooth. In the embodiment shown in FIG. 2, the sample 2 is disposed between the second and third teeth. However, when the sample is disposed between the second and third teeth, a rotating shaft of a sample goniometer 3 and the incident X-ray are not at right angles to each other. Thus, there arises a problem that incident angles differ depending on locations. Therefore, in FIG. 4, adjustment is made so as to set the rotating shaft of the sample goniometer 3 and the incident X-ray at right angles to each other by removing the center of the second tooth, placing film stacks 4 between the first and second teeth, and placing an exposed substrate 5 between the second and third teeth.

The sample 2 has a substrate obtained by sputter-depositing gold in a thickness of 3 μm on a silicon thin plate. Moreover, on the substrate, aluminum oxide is deposited in a thickness of about 1.5 μm as a thin film to be measured on the film stacks 4. In the exposed substrate 5 having no aluminum oxide deposited therein, the gold film is exposed. When the gold is deposited in the thickness of about 3 μm, the gold film can be treated the same as a gold substrate since the X-ray does not reach the silicon therebelow. The sample 2 is fixed on the sample goniometer 3 and adjusted so as to make the incident X-ray 1 incident on the sample 2 at 0.3°.

The incident X-ray 1 made incident on the sample 2 at 0.3° is totally reflected from the sample 2. The totally reflected X-ray is reflected from a reflection mirror 12 having gold deposited in a thickness of about 5 μm on a Si substrate. One of the amplitude-split incident X-rays 1 has its direction changed by the second tooth. Thereafter, the X-ray is reflected from the exposed substrate 5 of the sample 2 disposed between the second and third teeth and then reflected again from the reflection mirror 12. Thus, a reference wave 8 is obtained and made incident on the third tooth. The other amplitude-split incident X-ray 1 is reflected from the exposed substrate 5 and the film stacks 4 of the sample disposed between the first and second teeth. This reflective wave 13 is also reflected again from the reflection mirror 12 to obtain an objective wave 7. This objective wave 7 includes a reflective objective wave 14 from the film stacks and a reflective objective wave 9 from the exposed substrate. In this event, the X-ray 1 made incident on the sample 2 and the reflective X-ray are parallel to each other and at right angles to the rotating shaft of the sample goniometer 3. The objective wave 7 has its direction changed by the second tooth and then is made incident on the third tooth. The objective wave 7 and the reference wave 8 are allowed to overlap with each other at the third tooth, and interference patterns are measured by use of a high-resolution two-dimensional detector 10 (for example, a zooming tube). In this event, as in the case of the embodiment described above, if the reference wave 8 and the objective wave 7 are allowed to interfere with each other without making any adjustment, the same phase shift is set on the entire surface. Thus, there arises a situation where interference patterns are not visible. Therefore, by providing an acrylic prism 6 as a phase shifter on an optical path of the reference wave 8, the interference patterns can be obtained even in a state where there is no sample.

The interference patterns or information to be obtained are the same as those in the above embodiment and thus the same analysis method is adopted. However, this embodiment shows an analysis example using a thick sample such as the 1.5-μm aluminum oxide. An increase in the thickness of the sample reduces a ratio of a region where X-rays reflected from upper and lower surfaces overlap and interfere with each other with respect to a reflective X-ray flux. Moreover, when the synchrotron radiation source in the PF or a sealed-off tube type X-ray source is used, a coherence length is several μm and thus interference is unlikely to occur. Therefore, even if the X-ray reflectivity from the 1.5-μm aluminum oxide is measured, a vibrational structure of the film thickness cannot be seen in the X-ray reflectivity. However, in this embodiment, adjustment can be made so as to allow the reference wave 8 and the reflective objective wave 14 from film stacks to interfere with each other by use of the reflection mirror 12. Thus, the interference patterns can be measured even from the 1.5-μm aluminum oxide.

With reference to FIG. 6, analysis of the interference pattern obtained will be described. In the case of the thick sample such as that used in this embodiment, a phase shift between the reflective objective wave 9 from the exposed substrate and the reflective objective wave 14 from film stacks is set to $2\pi$ or more. Thus, analysis with one incident angle using the equation (1) cannot be performed. When the sample is thick, the phase is shifted by about $\pi$ to $2\pi$ even if the incident angle is changed by about 0.001°. Therefore, $\theta_1=0.3°$ and $\theta_2=0.301°$. The interference patterns are measured with the two angles. A change in an optical length due to a change in the incident angle is offset by setting a phase of the reflective objective wave 14 from the film stacks to have a relative value to the reflective objective wave 9 from the exposed substrate. In the case of this embodiment, $(\Delta L_2-\Delta L_1)/L$ is 0.495. Calculation using the equation (2) leads to d=1418 nm. This embodiment theoretically enables measurement of the layer thickness of about 10 μm. However, the layer thickness that can be actually measured is about 2 μm due to a problem such as that visibility of the interference patterns is lowered by absorption at the sample.

As described above, this embodiment enables measurement of the phase of the reflective X-ray from the X-ray source having a small coherence length and also enables analysis of layer thicknesses of the film stacks.

Lastly, description will be given of an embodiment of analysis of a sample including two layers stacked. The sample has a substrate obtained by sputter-depositing gold in a thickness of 3 μm on a silicon thin plate. Moreover, on the substrate, tantalum is deposited in a thickness of about 5 nm as a thin film to be measured on film stacks. In an exposed substrate 5 having no tantalum deposited thereon, the gold film is exposed. When the gold is deposited in the thickness of about 3 μm, the gold film can be treated the same as a gold substrate since the X-ray does not reach the silicon therebelow. Since the tantalum is oxidized naturally, oxidized tantalum film is formed in the thickness of about 3 nm. As to the incident X-ray made incident on the sample at 0.5°, interference patterns are measured at a position where a totally reflective objective wave from the sample and a wavefront-split or amplitude-split reference wave overlap with each other. FIG. 6 shows a schematic diagram of the interference patterns to be obtained. The objective wave and the reference wave overlap with each other to form the interference patterns. Under this incident angle condition, following interference patterns are obtained. Specifically, one of the interference patterns is obtained by overlapping the reference wave and an objective wave, that is an interference wave of the X-ray reflected from a sample surface. The other one of the interference patterns is obtained by overlapping the reference wave and an objective wave, that is the X-ray reflected from the substrate exposed portion of the sample. A difference between the interference patterns is a phase shift $\Delta L$ therebetween. The phase shift is obtained as $\Delta L/L=0.974$ when normalized by one cycle length of the interference pattern. Calculation according to the equation (8) leads to the same calculation formula as the equation (1). Thus, the overall thickness of the sample is obtained as d=5.581 nm.

Next, when the incident angle is reduced to 0.3°, following interference patterns are obtained. Specifically, one of the interference patterns is obtained by overlapping the reference wave and an objective wave, that is an interference wave of the X-ray reflected from the sample surface and a tantalum/tantalum oxide interface. The other one of the interference patterns is obtained by overlapping the reference wave and an objective wave, that is the X-ray reflected from the substrate exposed portion of the sample. A phase shift between the interference patterns is obtained as $\Delta L/L=0.364$ when normalized by one cycle length of the interference pattern. According to the equation (8), a thickness of the tantalum oxide film is obtained as d=3.476 nm. Here, the description has been given of calculation of layer thicknesses of multi-layer stacks by taking the same procedures as those in Embodiment 1. Meanwhile, measurement of interference patterns by setting the incident angle to 0.2° also enables analysis that does not require accuracy of an absolute value of the incident angle as shown in the other embodiment. As described above, each of layer thicknesses of multi-layer stacks can be analyzed by measuring the interference patterns at more measurement points than the number of interfaces included in the film stacks and by utilizing the equations (7) and (8).

As described above, this embodiment enables measurement of the phase of the reflective X-ray and analysis of layer thicknesses of the film stacks. Moreover, amplitude reflectivity from layer thicknesses of 1 to 2-μm thick film stacks can be measured even from a thin film thinner than 1 nm, which has been hard to inspect by use of the conventional X-ray reflectivity method. Thus, the layer thicknesses of the film stacks can be measured with high accuracy.

DESCRIPTION OF SYMBOLS

1. Incident X-ray
2. sample
3. sample goniometer
4. film stacks
5. exposed substrate
6. prism
7. objective wave
8. reference wave
9. reflective objective wave from substrate
10. X-ray imaging detector
11. amplitude splitting interferometer
12. reflection mirror
13. reflective X-ray
14. reflective objective wave from film stacks
15. three cycle length of interference pattern for reflective X-ray from exposed substrate 16. three cycle length of interference pattern for reflective X-ray from film stacks
17. phase shift
18. phase shift in incident angle of $\theta_2$

What is claimed is:

1. A layer thickness measurement method comprising the steps of:
    making an X-ray incident on a sample having multi-layer stacks formed on a substrate with the substrate partially exposed;
    using the X-ray specular-reflected from the exposed substrate in the sample as a reference wave and using the X-ray specular-reflected from the multi-layer stacks and the exposed substrate in the sample as an objective wave;
    bending the reference wave by use of a prism to interfere with the objective wave;
    measuring a phase shift between an interference pattern of the reference wave and an objective wave specular-reflected from the exposed substrate in the sample and an interference pattern of the reference wave and an objective wave specular-reflected from the multi-layer stacks in the sample; and
    obtaining layer thicknesses of the multi-layer stacks by use of the phase shift.

2. The layer thickness measurement method according to claim 1, wherein
    an incident angle of the X-ray to the sample is changed within a range of 0.01° to 1°.

3. The layer thickness measurement method according to claim 1, wherein
    the layer thicknesses of the entire multi-layer stacks are obtained, by utilizing the fact that one cycle difference is a wavelength of the incident X-ray, from a positional difference between the interference pattern of the reference wave and the objective wave specular-reflected from the exposed substrate in the sample and the interference pattern of the reference wave and the objective wave specular-reflected from the multi-layer stacks in the sample.

4. The layer thickness measurement method according to claim 1, wherein
    the layer thicknesses of the multi-layer stacks are obtained by changing the incident angle of the X-ray by at least once plus the number of films constituting the multi-layer stacks to measure a positional change between the interference pattern of the reference wave and the objective wave specular-reflected from the exposed substrate in the sample and the interference pattern of the reference wave and the objective wave specular-reflected from the multi-layer stacks in the sample and by analyzing a change in an optical length occurring with the change in the incident angle by use of positional movement of the interference patterns.

5. The layer thickness measurement method according to claim 1, wherein
    when the multi-layer stacks include thin films each having a thickness of not more than 2 μm, the layer thicknesses of the multi-layer stacks are obtained by changing the incident angle of the X-ray by at least once plus the number of the thin films constituting the multi-layer stacks to measure a change in the interference pattern between the X-ray specular-reflected from a multi-layer stack surface of the sample and the X-ray specular-reflected from an interface in the multi-layer stacks and by analyzing a change in an optical length occurring with the change in the incident angle by use of positional movement of the interference patterns.

6. A layer thickness measurement method comprising the steps of:
    disposing, in an amplitude splitting interferometer, a sample having multi-layer stacks formed on a substrate with the substrate partially exposed and a sample goniometer having a reflection mirror fixed thereto, the reflection mirror reflecting an X-ray reflected from the sample;
    using the X-ray specular-reflected from the exposed substrate in the sample and then specular-reflected from the reflection mirror as a reference wave, using the X-ray specular-reflected from the multi-layer stacks and the exposed substrate in the sample and then specular-reflected from the reflection mirror as an objective wave, and allowing the two waves to interfere with each other;
    measuring a phase shift between an interference pattern of the reference wave and an objective wave specular-reflected from the exposed substrate in the sample and then specular-reflected from the reflection mirror and an interference pattern of the reference wave and an objective wave specular-reflected from the multi-layer stacks in the sample and then specular-reflected from the reflection mirror; and
    obtaining layer thicknesses of the multi-layer stacks by use of the phase shift.

7. The layer thickness measurement method according to claim 6, wherein
    an incident angle of the X-ray to the sample is changed within a range of 0.01° to 1°.

8. The layer thickness measurement method according to claim 6, wherein
    the layer thicknesses of the entire multi-layer stacks are obtained, by utilizing the fact that one cycle difference is a wavelength of the incident X-ray, from a positional difference between the interference pattern of the reference wave and the objective wave specular-reflected from the exposed substrate in the sample and then specular-reflected from the reflection mirror and the interference pattern of the reference wave and the objective wave specular-reflected from the multi-layer stacks in the sample and then specular-reflected from the reflection mirror.

9. The layer thickness measurement method according to claim 6, wherein
    the layer thicknesses of the multi-layer stacks are obtained by changing the incident angle of the X-ray by at least once plus the number of thin films constituting the multi-layer stacks to measure a positional change between the interference pattern of the reference wave and the objective wave specular-reflected from the exposed substrate in the sample and then specular-reflected from the reflection mirror and the interference pattern of the reference wave and the objective wave specular-reflected from the multi-layer stacks in the sample and then specular-reflected from the reflection mirror and by analyzing a change in an optical length occurring with the change in the incident angle by use of positional movement of the interference patterns.

10. The layer thickness measurement method according to claim 6, wherein
    when the multi-layer stacks include thin films each having a thickness of not more than 2 μm, the layer thicknesses of the multi-layer stacks are obtained by changing the incident angle of the X-ray by at least once plus the number of the thin films constituting the multi-layer stacks to measure a change in the interference pattern between the X-ray specular-reflected from a multi-layer stack surface and then specular-reflected from the reflection mirror and the X-ray specular-reflected from an interface in the multi-layer stacks and then specular-reflected from the reflection mirror and by analyzing a change in an optical length occurring with the change in the incident angle by use of positional movement of the interference patterns.

* * * * *

UNITED STATES PATENT AND TRADEMARK OFFICE
CERTIFICATE OF CORRECTION

PATENT NO. : 7,751,527 B2
APPLICATION NO. : 12/292178
DATED : July 6, 2010
INVENTOR(S) : Ueda et al.

Page 1 of 1

It is certified that error appears in the above-identified patent and that said Letters Patent is hereby corrected as shown below:

On the Title Page insert Item

--(30) Foreign Application Priority Data

January 16, 2008   (JP) .........2008-007115--

Signed and Sealed this
First Day of March, 2011

David J. Kappos
*Director of the United States Patent and Trademark Office*